(12) United States Patent
Kumaravel et al.

(10) Patent No.: US 9,335,332 B2
(45) Date of Patent: May 10, 2016

(54) NICOTINAMIDE PHOSPHORIBOSYLTRANSFERASE (NMPRTASE) INHIBITOR FOR GLIOMA THERAPY

(75) Inventors: Somasundaram Kumaravel, Bangalore (IN); Nagasuma Chandra, Bangalore (IN)

(73) Assignee: COUNCIL OF SCIENTIFIC AND INDUSTRIAL RESEARCH, New Delhi (IN)

( * ) Notice: Subject to any disclaimer, the term of this patent is extended or adjusted under 35 U.S.C. 154(b) by 841 days.

(21) Appl. No.: 13/695,936

(22) PCT Filed: Mar. 31, 2011

(86) PCT No.: PCT/IB2011/000696
§ 371 (c)(1),
(2), (4) Date: Jun. 28, 2013

(87) PCT Pub. No.: WO2011/121434
PCT Pub. Date: Oct. 6, 2011

(65) Prior Publication Data
US 2013/0274286 A1    Oct. 17, 2013

(30) Foreign Application Priority Data
Apr. 1, 2010    (IN) .............................. 811/DEL/2010

(51) Int. Cl.
*A61K 31/47*      (2006.01)
*G01N 33/94*    (2006.01)
*A61K 31/4725*  (2006.01)

(52) U.S. Cl.
CPC ............ *G01N 33/94* (2013.01); *A61K 31/4725* (2013.01)

(58) Field of Classification Search
CPC .... A61K 31/47; A61K 31/4725; G01N 33/94
USPC ................................ 514/309; 506/8; 546/141
See application file for complete search history.

(56) References Cited

FOREIGN PATENT DOCUMENTS

| WO | 2007/012937 A2 | 2/2007 |
|---|---|---|
| WO | 2009/000552 A2 | 12/2008 |

OTHER PUBLICATIONS

Nagasuma Chandra et al., "Virtual Screening, Identification and Experimental Testing of Novel Inhibitors of PBEF1/Visfatin/NMPRTase for Glioma Therapy", Journal of Clinical Bioinformatics, Jan. 20, 2011, pp. 1-12, vol. 1, No. 5.
International Search Report for Entry of PCT/IB2011/000696 dated Jul. 12, 2011.

*Primary Examiner* — Jason Sims
*Assistant Examiner* — Ibrahim D Bori
(74) *Attorney, Agent, or Firm* — Sughrue Mion, PLLC (57) ABSTRACT

The present invention relates to identification of a compound which inhibits the enzyme NMPRTase and glioma cancer cell growth and further used for glioma therapy. Pre-B-cell colony enhancing factor 1 gene (PBEF1) encodes nicotinamide phosphoribosyltransferase (NMPRTase), which catalyzes the rate limiting step in the salvage pathway of NAD metabolism in mammalian cells. PBEF1 transcript and protein levels have been shown to be elevated in glioblastoma and a chemical inhibitor of NMPRTase has been shown to specifically inhibit cancer cells. Here a structure based drug discovery approach has been reported with an aim to develop novel inhibitors for glioblastoma therapy. Present invention relates to virtual screening using docking of ligands from a large library of 13,000 compounds against NMPRTase as the macromolecular target resulting in short listing of 34 possible ligands, of which six were tested experimentally, using the NMPRTase enzyme inhibition assay and further with the glioma cell viability assays. Of these, two compounds were found to be significantly efficacious in inhibiting the conversion of nicotinamide to NAD, and out of which one compound, 3-amino-2-benzyl-7-nitro-4-(2-quinolyl-)-1,2-dihydroisoquinolin-1-one, was found to inhibit the growth of a PBEF1 over expressing glioma derived cell line U87 also.

5 Claims, 4 Drawing Sheets

NICOTINAMIDE PHOSPHORIBOSYLTRANSFERASE (NMPRTASE) INHIBITOR FOR GLIOMA THERAPY

FIELD OF THE INVENTION

The present invention relates to a method for identification of a compound which inhibits both the enzyme NMPRTase and glioma cancer cell growth, and therefore could be used for glioma therapy. More particularly, the present invention relates to the treatment of cancer.

BACKGROUND OF THE INVENTION

Gliomas are primary malignant tumors, originating in the brain, and account for 80% of adult primary brain tumors. Malignant gliomas which includes glioblastoma are the most common and fatal intracranial tumors (Furnari, F. B.; Fenton, T.; Bachoo, R. M.; Mukasa, A.; Stommel, J. M.; Stegh, A.; Hahn, W. C.; Ligon, K. L.; Louis, D. N.; Brennan, C.; Chin, L.; DePinho, R. A.; Cavenee, W. K. Malignant astrocytic glioma: genetics, biology, and paths to treatment. *Genes Dev* 2007, 21, 2683-710). The prognosis for patients with glioblastoma multiforme, a virulent variety of the disease is rather poor, with a median survival of less than one year (Legler, J. M.; Ries, L. A.; Smith, M. A.; Warren, J. L.; Heineman, E. F.; Kaplan, R. S.; Linet, M. S. Cancer surveillance series [corrected]: brain and other central nervous system cancers: recent trends in incidence and mortality. *J Natl Cancer Inst* 1999, 91, 1382-90). One of the most important challenges we face today is to develop novel methods of therapy. Several altered genes and pathways have been target of designing novel therapeutic strategies. Inventors had earlier reported PBEF1/NMPRTase/Visfatin as a potential malignant astrocytoma/glioblastoma serum marker with prognostic value (Reddy, P. S.; Umesh, S.; Thota, B.; Tandon, A.; Pandey, P.; Hegde, A. S.; Balasubramaniam, A.; Chandramouli, B. A.; Santosh, V.; Rao, M. R.; Kondaiah, P.; Somasundaram, K. PBEF1/NAmPRTase/Visfatin: a potential malignant astrocytoma/glioblastoma serum marker with prognostic value. *Cancer Biol Ther* 2008, 7, 663-8). PBEF1 transcript and protein levels were found to be elevated in malignant gliomas, in particular glioblastoma tissue samples and also in the corresponding patients serum samples (Reddy, P. S.; Umesh, S.; Thota, B.; Tandon, A.; Pandey, P.; Hegde, A. S.; Balasubramaniam, A.; Chandramouli, B. A.; Santosh, V.; Rao, M. R.; Kondaiah, P.; Somasundaram, K. PBEF1/NAmPRTase/Visfatin: a potential malignant astrocytoma/glioblastoma serum marker with prognostic value. *Cancer Biol Ther* 2008, 7, 663-8). PBEF1 encodes Nicotinamide phosphoribosyltransferase (NMPRTase), which catalyses the rate limiting step in the salvage pathway of NAD (Nicotinamide Adenine Diphosphate) metabolism in mammalian cells. While the role of PBEF1 over expression in glioma is not understood, it may regulate signaling pathways related to apoptosis and chemosensitivity (Jia, S. H.; Li, Y.; Parodo, J.; Kapus, A.; Fan, L.; Rotstein, O. D.; Marshall, J. C. Pre-B cell colony-enhancing factor inhibits neutrophil apoptosis in experimental inflammation and clinical sepsis. *J Clin Invest* 2004, 113, 1318-27; Yang, H.; Yang, T.; Baur, J. A.; Perez, E.; Matsui, T.; Carmona, J. J.; Lamming, D. W.; Souza-Pinto, N. C.; Bohr, V. A.; Rosenzweig, A.; de Cabo, R.; Sauve, A. A.; Sinclair, D. A. Nutrient-sensitive mitochondrial NAD+ levels dictate cell survival. *Cell* 2007, 130, 1095-107; Folgueira, M. A.; Carraro, D. M.; Brentani, H.; Patrao, D. F.; Barbosa, E. M.; Netto, M. M.; Caldeira, J. R.; Katayama, M. L.; Soares, F. A.; Oliveira, C. T.; Reis, L. F.; Kaiano, J. H.; Camargo, L. P.; Vencio, R. Z.; Snitcovsky, I. M.; Makdissi, F. B.; e Silva, P. J.; Goes, J. C.; Brentani, M. M. Gene expression profile associated with response to doxorubicin-based therapy in breast cancer. *Clin Cancer Res* 2005, 11, 7434-43). A potent inhibitor of NMPRTase enzyme, FK866, has been shown to reduce cellular NAD+, inhibit growth of PBEF1 over expressing cells and induce apoptosis in tumors (Hasmann, M.; Schemainda, I. FK866, a highly specific noncompetitive inhibitor of nicotinamide phosphoribosyltransferase, represents a novel mechanism for induction of tumor cell apoptosis. *Cancer Res* 2003, 63, 7436-42). The crystal structures of free NMPRTase, NMPRTase bound to NMN, and NMPRTase bound to the inhibitor FK866 have recently been reported (Khan, J. A.; Tao, X.; Tong, L. Molecular basis for the inhibition of human NMPRTase, a novel target for anticancer agents. *Nat Struct Mol Biol* 2006, 13, 582-8). FK866 is a potent small-molecule inhibitor of human NMPRTase, and the consequent reduction in NAD levels can cause apoptosis of tumor cells while having little (toxic) effects on normal cells (Hasmann and Schemainda, 2003). FK866 also turns out to be the only promising inhibitor known, for the enzyme. The available structures provide a basis for understanding substrate specificity, mechanism of enzyme action and provide a framework for design of novel NMPRTase inhibitors.

Here inventors report virtual screening of a large library of compounds and short listing of 6 candidate molecules that are likely to bind to NMPRTase. These compounds were subsequently tested experimentally for their ability to (a) inhibit the conversion of Nicotinamide to NAD by NMPRTase and (b) inhibit efficiently the growth of NMPRTase over expressing glioblastoma derived cell line U87. Based on these studies, a promising lead compound has been identified.

Currently there are only few compounds known to inhibit NMPRTase activity. So it is essential to search for more potential compounds for glioblastoma therapy.

Using Bioinformatics approach, the inventors screened 13214 compounds to identify possible candidates as inhibitors for NMPRTase enzyme, and found, 3-amino-2-benzyl-7-nitro-4-(2-quinolyl)-1,2-dihydroisoquinolin-1-one as a promising lead compound that inhibits NMPRTase and glioma cell growth.

OBJECT OF THE INVENTION

The main object of the present invention is to develop a method for identification of a compound useful in Glioma Therapy.

Another object of the present invention is to provide a method of treating glioblastoma multiforme using identified compound.

SUMMARY OF THE PRESENT INVENTION

The present invention relates to a method for identification of a compound which inhibits both the enzyme NMPRTase and glioma cancer cell growth, and therefore could be used for glioma therapy. More particularly, the present invention relates to the treatment of cancer.

Using Bioinformatics approach 13214 compounds were screened to identify potential inhibitor for NMPRTase enzyme and 3-amino-2-benzyl-7-nitro-4-(2-quinolyl)-1,2-dihydroisoquinolin-1-one comes out to be a promising lead compound that inhibits NMPRTase and glioma cell growth.

In an embodiment of the present invention, a method of identifying a compound that inhibits the activity of nicotinamide phosphoribosyl transferase enzyme useful for regulating growth of glioma cells, wherein the method comprises:
a) virtual screening of ligand library to identify possible compounds on the basis of Lipinski guidelines for druglikeness;
b) docking the dataset as obtained in step (a) against NMPRTase, 2GVG (NMPRTase complex with the reaction product NMN) and 2GVJ (NMPRTase bound to the FK866 inhibitor);
c) identifying possible compounds as obtained in step (b) on the basis of docked poses with binding energy lower than the cut-off criteria and cluster size greater than the cut-off;
d) experimental testing of the shortlisted compounds as obtained in step (c) for the inhibition of NMPRTase activity and growth of glioma cells.
e) identifying 3-amino-2-benzyl-7-nitro-4-(2-quinolyl)-1,2-dihydroisoquinolin-1-one having formula A from the shortlisted compounds as obtained in step (d) as the possible inhibitor of NMPRTase and glioma.

Formula A

In other embodiment of the present invention, the energy cut-off value is less than −8.5 kcal/mol and cluster size cut-off value is more than 15.

In yet another embodiment of the present invention, the glioma cells used is gliomablastoma cell line U87.

In yet another embodiment of the present invention, the compound 3-amino-2-benzyl-7-nitro-4-(2-quinolyl)-1,2-dihydroisoquinolin-1-one inhibits glioma derived cell line U87 with $IC_{50}$ of 325 μM in vitro.

In yet another embodiment of the present invention, a composition consisting of the identified compound 3-amino-2-benzyl-7-nitro-4-(2-quinolyl)-1,2-dihydroisoquinolin-1-one is administered to the patient suffering from cancer.

In yet another embodiment of the present invention, the cancer is glioblastoma multiforme.

In still another embodiment of the present invention, the compound 3-amino-2-benzyl-7-nitro-4-(2-quinolyl)-1,2-dihydroisoquinolin-1-one is used for the treatment of cancer.

BRIEF DESCRIPTION OF FIGURES

FIG. 1(a)-FIG. 1(i):
Docked poses for the potential lead compounds identified after virtual screening as shown in FIG. 1(a)-FIG. 1(f). The first binding mode is shown for all compounds, whereas the second mode is shown only for compound 5, which was the most efficacious lead molecule among the six,
FIG. 1(a): compound 1,
FIG. 1(b): compound 2,
FIG. 1(c): compound 3,
FIG. 1(d): compound 4,
FIG. 1(e): compound 5,
FIG. 1(f): compound 6, all in mode 1. The crystallographically observed poses of NMN and FK866 are shown in FIG. 1(g) and FIG. 1(h) respectively.

FIG. 2(A) and FIG. 2 (B)

FIG. 3(A) and FIG. 3(B)

FIG. 5(a)-FIG. 5(f):
Crystallographically observed binding modes of the known and new ligands in NMPRTase as shown in FIG. 5(a)-FIG. 5(f); FIG. 5(a) NMN, FIG. 5(b) FK866, and docked binding modes of compounds 4 and 5; FIG. 5(c) and FIG. 5(e) panels indicate the first binding modes of compounds 5 and 4 respectively while panels; FIG. 5(d) and FIG. 5(f) indicate the second binding modes of compounds 5 and 4 respectively. The ligands are in ball and stick representation and colored by standard atom types; the A chain residues of the site are shown in red and C chain residues are in blue, in all the panels.

DETAILED DESCRIPTION OF THE PRESENT INVENTION

Accordingly, the present invention provides a method of identifying a compound useful as glioblastoma therapeutic agent, use of such compound for Glioma therapy and method of treating the glioblastoma multiforme.

In one embodiment, the method of identifying a compound comprises the steps of:
a. virtual screening of ligand library to identify possible compounds on the basis of Lipinski guidelines for druglikeness;
b. docking the dataset as obtained in step (a) against NMPRTase, 2GVG (NMPRTase complex with the reaction product NMN) and 2GVJ (NMPRTase bound to the FK866 inhibitor);
c. identifying possible compounds as obtained in step (b) on the basis of docked poses with binding energy lower than the cut-off criteria and cluster size greater than the cut-off;

d. experimental testing of the shortlisted compounds as obtained in step (c) for the inhibition of NMPRTase activity and growth of glioma cells.
e. identifying 3-amino-2-benzyl-7-nitro-4-(2-quinolyl)-1,2-dihydroisoquinolin-1-one having formula A from the shortlisted compounds as obtained in step (d) as the possible inhibitor of NMPRTase and glioma.

Formula A

The shortlisted compounds comprises Dipotassium 9-oxo-9H-fluorene-2,7-disulfonate, Ethyl-5-amino-6-cyano-7-(2-furyl)-4-oxo-3-phenyl-3,4-dihydro-1-phthalazinecarboxylate, 1,[3,5-Di(2H-1,2,3-benzotriazol-2-yl)-2,4-dihydroxyphenyl]ethan-1-one, 7a-methyl-2,4,5-triphenyl-7,7a-dihydrocyclopenta[b]pyran-7-one, 3-amino-2-benzyl-7-nitro-4-(2-quinolyl)-1,2-dihydroisoquinolin-1-one, N-[(5-methyl-2-phenyl-2H-1,2,3-triazol-4-yl)methyl]-2H-chromene-3-carboxamide.

In an aspect, the identified compound of formula A acts as inhibitor of NMPRTase (nicotinamide phosphoribosyl transferase) enzyme useful for regulating growth of glioma cells.

In one aspect, for the identification of said compounds, the binding energy cut-off value is less than −8.5 kcal/mol and cluster size cut-off value is more than 15.

In another aspect, the said glioma cell used is gliomablastoma cell line U87.

In yet another aspect, the identified compound inhibits glioma derived cell line U87 with $IC_{50}$ of 325 µM in vitro.

In an embodiment, the invention provides a compound, 3-amino-2-benzyl-7-nitro-4-(2-quinolyl)-1,2-dihydroisoquinolin-1-one, of formula A for use in Glioma therapy.

Formula A

The compound of formula A inhibits the activity of nicotinamide phosphoribosyl transferase enzyme useful for regulating growth of glioma cells.

In an embodiment, the invention provides method for treating glioblastoma multiforme, wherein the said method comprising administrating to the patient suffering from glioblastoma multiforme cancer the said compound of formula A.

Formula A

Further, a composition consisting of the said identified compound of formula A is administered to the patient suffering from cancer such glioblastoma multiforme. The said composition comprises of pharmaceutically acceptable excipients, carriers and diluents.

Glioma includes 1. Diffuse Oligodendroglioma (DO; WHO Gr. II), 2. Anaplastic Oligodendroglioma (AO; WHO Gr. III), 3. Diffuse astrocytoma (DA; WHO Gr. II), 4. Anaplastic astrocytoma (AA; WHO Gr. III) and 5. Glioblastoma (GBM; WHO Gr. IV). GBMs are of two types: primary GBM (de novo type), which manifests in older patients (mean age: 55 yrs), as an aggressive, highly invasive tumor, usually without any evidence of prior clinical disease after a short clinical history of less than 3 months; Secondary GBM (progressive type) is usually seen in younger patients (mean age: 40 yrs) and develops more slowly by malignant progression from diffuse (WHO Grade II) or anaplastic astrocytoma (WHO Grade III).

NAD biosynthesis has been shown to be activated in cancers (Yang et al., 2007). NAD+, in addition to its role as a redox cofactor, is also used as a substrate in several biochemical reactions including mono- and poly-ADP (Adenosine diphosphate) ribosylation (ART (agouti-related protein) and PARP (Poly ADP ribose polymerase) catalyzed), protein deacetylation and ADP-ribose cyclization. NMPRTase catalyzes the conversion of free nicotinamide to nicotinamide mononucleotide (NMN), which is a key step in the salvage pathway of NAD+. Expression levels of NMPRTase (also known as visfatin/Pre B-cell enhancing factor1 (PBEF1)), was found to be upregulated in colorectal cancers (Jia et al., 2004), suggesting that NMPRTase may be crucial for maintaining cellular NAD levels in tumors. Microarray analyses of glioma cells (grade II to IV) versus normal brain glial cells has identified differential expression of NMPRTase in glioma with 2-5 fold upregulation in glioma cells, depending on the grade of the tumor (increased expression of NMPRTase with greater progression of the disease, Grade IV>Grade III>Grade II). Observation of increased rates of NAD metabolism in glioma, suggests that the cancer cells may be critically dependent upon metabolites produced in the pathway, and presents a possible strategy to counter the disease, through the inhibition of key enzymes in the pathway.

The crystal structures of free NMPRTase, NMPRTase bound to NMN, and NMPRTase bound to the inhibitor FK866 have recently been reported (Khan, et al., 2006). FK866 is a potent small-molecule inhibitor of human NMPRTase, and the consequent reduction in NAD levels can cause apoptosis of tumor cells while having little (toxic) effects on normal cells (Hasmann and Schemainda, 2003). FK866 also turns out to be the only promising inhibitor known, for the enzyme. The structures provide a basis for understanding substrate specificity, mechanism of enzyme action and provide a framework for design of novel NMPRTase inhibitors.

The inventive method involves the use of structure based drug discovery approach to find potential NMPRTase inhibitor which is further used as novel inhibitor of glioblastoma. An extremely useful step in the rational design of inhibitors is to utilize the three dimensional structural information of the target protein and identify a possible lead compound from large libraries of compounds. Although several docking algorithms have been developed (Ewing, T. J. A.; Kuntz, I. D. Critical evaluation of search algorithms for automated molecular docking and database screening, *Journal of Computational Chemistry* 1997, 18, 1175-1189), (Garrett, M. M.; David, S. G.; Robert, S. H.; Ruth, H.; William, E. H.; Richard, K. B.; Arthur, J. O. Automated docking using a Lamarckian genetic algorithm and an empirical binding free energy function. *Journal of Computational Chemistry* 1998, 19, 1639-1662), virtual screening of potential ligands to a given protein at the three dimensional level has generally been prohibitive on a routine scale, owing to the amount of computing time that is required. However, inventors have recently developed a parallel version of a popular docking algorithm—Autodock (Ruben, A.; Maxim, T.; Dmitry, K. ICM—A new method for protein modeling and design: Applications to docking and structure prediction from the distorted native conformation. *Journal of Computational Chemistry* 1994, 15, 488-506) and have implemented this on an IBM Bluegene supercomputer (Khodade, P.; Prabhu, R.; Chandra, N.; Raha, S.; Govindarajan, R. Parallel implementation of AutoDock. *Journal of Applied Crystallography* 2007, 40, 598-599), rendering the docking approach amenable for high throughput virtual screening. Here inventors report virtual screening of a large library of compounds and shortlisting of 6 candidate molecules that are likely to bind to NMPRTase. These compounds were subsequently tested experimentally for their ability to (a) inhibit the conversion of nicotinamide to NAD by NMPRTase and (b) inhibit efficiently the growth of a PBEF1 over expressing glioblastoma derived cell line U87. Based on these studies, a promising lead compound has been identified.

The inventive method includes virtual screening using docking of ligands from different libraries (n=13214) against NMPRTase as the macromolecular target resulted in identification of six potential lead compounds. Of these, two compounds inhibited NMPRTase in vitro and out of which one compound 3-amino-2-benzyl-7-nitro-4-(2-quinolyl)-1,2-dihydroisoquinolin-1-one also inhibited efficiently the growth of a PBEF1 over expressing glioma cell line U87. Thus, inventors have successfully used structure based drug discovery approach and identified a promising lead compound that inhibits NMPRTase and glioma cell growth.

Pre-B-cell colony enhancing factor 1 gene (PBEF1) encodes nicotinamide phosphoribosyltransferase (NMPRTase), which catalyses the rate limiting step in the salvage pathway of NAD (Nicotinamide adenine dinucleotide) metabolism in mammalian cells. PBEF1 transcript and protein levels have been shown to be elevated in glioblastoma and a chemical inhibitor of NMPRTase has been shown to specifically inhibit cancer cells. Here inventors report a structure based drug discovery approach with an aim to develop novel inhibitors for glioblastoma therapy. This invention relates to virtual screening using docking of ligands from a large library of 13,000 compounds against NMPRTase as the macromolecular target resulting in short listing of 34 possible ligands, of which six were tested experimentally, using the NMPRTase enzyme inhibition assay and further with the glioma cell viability assays. Of these, two compounds were found to be significantly efficacious in inhibiting the conversion of nicotinamide to NAD, and out of which one compound, 3-amino-2-benzyl-7-nitro-4-(2-quinolyl-)-1,2-dihydroisoquinolin-1-one, was found to inhibit the growth of a PBEF1 over expressing glioma derived cell line U87 also. Thus, we have successfully used structure based drug discovery approaches by computational identification and experimental verification of a promising lead compound for inhibition of NMPRTase and glioma cancer cell growth inhibition.

The following examples are given by way of illustration of the present invention and therefore should not be constructed to limit the scope of the present invention.

Example 1

Methods and Reagents

Virtual Screening:

Different steps involved in virtual screening are briefly described below:

a) Selection of Ligand Library and Preparation of Ligands and Protein:

In accordance with the inventive steps, virtual screening was performed to identify possible lead compounds from the Maybridge HitFinder™ database. The Maybridge HitFinder™ sets are structural representatives of larger non-redundant chemical libraries. This collection includes 14,400 compounds that represent the drug-like diversity of the Maybridge Screening Collection (56,000 compounds). All the screening compounds fit Lipinski guidelines for drug-likeness: partition coefficient log P≤5, H-bond donors≤5, H-bond acceptors≤10, molecular weight≤500 (Lipinski, C. A.; Lombardo, F.; Dominy, B. W.; Feeney, P. J. Experimental and computational approaches to estimate solubility and permeability in drug discovery and development settings. *Adv Drug Deliv Rev* 2001, 46, 3-26). The Maybridge HitFinder™ set was obtained from www.maybridge.com. The ligand files were prepared for docking using Schrodinger Ligprep software (LIGPREP http://www.schrodinger.com/ProductDescription.php?mID=6&sID=7&cID=0). In addition to generation of energy minimized 3D structures, Schodinger Ligprep was also used for addition of hydrogens and desalting of metal ions. The Ligparse module was used during Ligprep and the ligands with following properties were removed from the set: molecular weight less than 200, number of neutral acceptor groups greater than 10 and number of neutral donor groups greater than 5. A total of 13214 ligands were selected and retained out of the total 14,400 original ligands.

b) Docking:

The co-ordinates of the human NMPRTase (PDB (Protein databank)); 2GVG (it is a unique four letter code in PDB for NMPRTase complex with the reaction product nicotinamide mononucleotide (NMN)); 2GVJ (it is a unique four letter code in PDB for NMPRTase bound to the FK866 inhibitor) were obtained from PDB (www.rcsb.org). The protein file was prepared for docking by removal of water molecules, addition of polar hydrogens, removal of ligand and phosphate groups in active site, and addition of Kollman charges (Singh, U. C.; Peter, A. K. An approach to computing electrostatic charges for molecules. *Journal of Computational Chemistry* 1984, 5, 129-145). The macromolecule was treated to be completely rigid for all docking studies to reduce the extensive computational costs. A grid box encompassing both the NMN and FK866 sites (86×60×50; 0.375 Å spacing) was constructed and used for all the docking runs. Docking parameter files were prepared for each ligand using the following parameters: ga_pop_size 150; ga_num_evals 2500000; ga_num_generations 500; ga_run 100 and rmstol 1.0. ga refers to Genetic Algorithm that forms the cruz of the software. Ligand confirmations are treated as individuals in a population according to GA, and thus 150 individuals is the default population size that is considered. ga_num_evals refers to the number of evaluations of the GA run. An energy evaluation is performed every time the GA or the local search computes the fitness of a candidate docking. If there is a population of 150, as specified by the 'ga_pop_size' parameter, then every generation, there will be 150 energy evaluations to compute the fitness of all the members of the population. ga_num_generations refers to the GA number of generations. AutoDock stops a docking if either the maximum number of evaluations or the maximum number of generations is reached, whichever comes first. In this case, the docking would terminate based on reaching the maximum number of energy evaluations, namely 25 million evals, since there are fewer than 500 generations in these runs. ga_run refers to the number of runs or number of times a random seed is invoked to perform the ligand fit process. Each time it runs and performs the evaluations and generations on the specified set of individuals, it tries to capture the best fit having the lowest energy, thus in different runs we can expect different or the same binding interaction energy. Thus, more the number of GA runs, better the clustering and docking poses. Rmsdtol refers to the tolerance limit to the structural deviation of the observed poses of the ligand confirmations. Different confirmations of the ligand stand at fairly distant spacing in 3d space, and thus to obtain the clustering of the ligand confirmations as in the best pose, we impose a cut-off value of 1 A from the best pose.

The Maybridge HitFinder™ dataset was docked using the parallel version of AutoDock 3, available in the laboratory using 256 processors on an IBM cluster. This process greatly reduced the computational cost and time involved in virtual screening of the large dataset (~13214). Clustering was performed based on the similarity in binding modes and affinities in the run cycles. The Ligand Protein Contacts (LPC) (Sobolev, V.; Sorokine, A.; Prilusky, J.; Abola, E. E.; Edelman, M. Automated analysis of interatomic contacts in proteins. *Bioinformatics* 1999, 15, 327-32) was used for obtaining the interactions of docked ligand atoms with the macromolecule, hydrogen bonding, van der Waals contacts and the solvent accessible surface area.

c) Short Listing of Potential Leads:

In accordance with the inventive steps, the docking log files (.dlg) were parsed using in-house perl scripts to scan the clustering histograms, and identify ligands that have docked poses with binding energy lower than the cut-off criteria and cluster size greater than the cut-off. The cut-off values were obtained from docking the known inhibitor FK866, and product NMN, to the receptor, and retrieving the docking energy and cluster size values for poses that have least deviation from the crystal pose (RMSD (root mean square deviation)<1.0). Due to the availability of a newer version of AutoDock, the exercise was repeated for the short listed compounds with the same parameters using AutoDock4 (version 4.0.1).

Energy Minimization:

Minimization of the docked pose for those which agreed well with the scoring functions was done using CNS software suite (Brunger, A. T.; Adams, P. D.; Clore, G. M.; DeLano, W. L.; Gros, P.; Grosse-Kunstleve, R. W.; Jiang, J. S.; Kuszewski, J.; Nilges, M.; Pannu, N. S.; Read, R. J.; Rice, L. M.; Simonson, T.; Warren, G. L. Crystallography & NMR system: A new software suite for macromolecular structure determination. *Acta Crystallogr D Biol Crystallogr* 1998, 54, 905-21). Conjugate gradient method was used for minimization with flexibility allowed only for those atoms within the 6 A° radius of every atom of the ligand for 150 runs. The topology and parameter files for the compounds were obtained from XPLO-2D software (Kleywegt G J, Z. J., Kjeldgaard, M, Jones T A. Around O. In *International Tables for Crystallography, Vol. F. Crystallography of Biological Macromolecules*, Rossmann M G, A. E., Ed. Dordrecht: Kluwer Academic Publishers, The Netherlands: 2001; pp 353-356, 366 367). Molecular visualization tool Pymol[16] (DeLano, W. L. The PyMOL Molecular Graphics System www.pymol.org) was used to generate the images of the docked complexes.

Reagents and Cell Lines

Cancer cell lines U373, U138, LN229, U343, U87, U251, LN18, SW480, HaCaT and HBL100 cells were cultured in DMEM (Dulbecco's modified Eagle's medium) respectively with 10% Fetal bovine serum, penicillin and streptomycin at 37° C. in a humidified atmosphere with 5% $CO_2$. Normal brain tissue samples (anterior temporal lobe) obtained during surgery for intractable epilepsy was used as control samples. These samples were originally obtained as a part of an ongoing Council of Scientific and Industrial Research—New Millennium Indian Technology Leadership Initiative (CSIR-NMITLI) genomics program involving Sri Sathya Sai Institute of Higher Medical Sciences (SSIHMS) and National Institute of Mental Health and Neurosciences (NIMHANS), Bangalore, India. The above study has been scrutinized and approved by the ethics committee of the two clinical centers and patient consent was obtained prior to initiation of the study as per the IEC (Institutional Ethics Committee) guidelines and approval. The six best docked compounds were purchased from Maybridge, Thermo Fisher Scientific, UK. $C^{14}$-Nicotinamide (Specific activity 55 mCi/mmol) was purchased from American Radiolabeled Chemicals, USA.

RNA isolation and RT-qPCR: In accordance with the inventive steps, RNA isolation and RT-qPCR was carried out. Total RNA was extracted from the frozen tissue (normal brain tissue) and cancer cell lines by using the TRI reagent (Sigma). The RNA samples were quantified by measuring the absorbance using a spectrophotometer and visualized on a MOPS (3-(N-morpholino)propanesulfonic acid) formaldehyde gel for quality assurance. The relative quantification of the expression levels of selected genes was carried out using a two-step strategy: In the first step, cDNA was generated from RNA derived from different tissue samples using a cDNA archive kit (ABI PRISM); subsequently, real-time quantitative PCR was carried out in an ABI PRISM 7900 (Applied Biosystems) sequence detection system with the cDNA as template using PBEF1 specific primer set and a Dynamo kit containing SYBR green dye (Finnzymes). All measurements were made in triplicates. The genes GARS (glycyl-tRNA synthetase), AGPAT1 (1-acylglycerol-3-phosphate O-acyltransferase 1), ATP5G1 [ATP synthase, H+ transporting, mitochondrial F0 complex, subunit C1 (subunit 9)], and RPL35A (ribosomal protein L35a) were used as internal controls because their expression levels were found to be unaltered in microarray experiments. Delta-delta CT method was used for the calculation of ratios. Sequences of reverse transcription-PCR primers and conditions used will be provided on request.

Example 2

Western Blot Analysis

In accordance with the inventive steps, western analysis with Rabbit polyclonal antibody against GST-PBEF1 (glutathione S-transferase-Pre-B cell colony-enhancing factor 1) raise in the laboratory using standard immunization protocol and antitubulin antibody has been performed.

Example 3

NMPRTase Assay

In accordance with the inventive steps, the measurement of NMPRTase activity was carried. To prepare cytoplasmic extract, as source of NMPRTase, logarithmically growing U87 glioblastoma cells were collected by centrifugation and washed three times with $Ca^{2+}$, $Mg^{2+}$ free PBS. The cells pellet (2 to $3 \times 10^7$ cells) was suspended and lysed in 1 mL of 0.01 M $NaH_2PO_4$ (pH 7.4) by one round of freezing and slow thawing. The clear supernatant was recovered on ice after centrifugation at 23,000×g at 0° C. for 90 mins. 70 mL of 1% protamine sulfate were added per ml of supernatant and incubated for 15 min on ice, followed by centrifugation at 23,000×g at 0° C. for 30 mins. The final supernatant was stored in small aliquots at −80° C. The NMPRTase activity was determined in 0.5 ml of reaction solution consisting of 5 mM MgCl2, 2 mM ATP, 0.5 mM phosphoribosyl PPI (pyrophosphate), 0.1 mM 14[C]-nicotinamide (specific activity: 50 mCi/mmol; American Radiolabeled Chemicals, Inc.) and 50 mM Tris (pH 8.8) at 37° C. The reaction was started by adding 100 µl of cell extract and stopped after 1 hr with excess of cold nicotinamide and heating (2 min, 105° C.). The precipitate was removed by centrifugation at 2500×g at 4° C. for 10 min and the supernatant was stored at −20° C. The 14[C]-labeled components in the cell extracts were separated and identified using thin-layer chromatography (cellulose/1 M ammonium sulphate:ethanol (3:7). The chromatograms were run and exposed to imaging plates (Fuji) read using Phosphoimger (Fuji) the 14[C]-labeled NAD was quantified using Alpha Innotec software.

Example 4

MTT ([3-(4,5-Dimethylthiazol-2-yl)-2,5-Diphenyltetrazolium Bromide]) assay

In accordance with the inventive steps, MTT assay was performed (Das, S.; El-Deiry, W. S.; Somasundaram, K. Efficient growth inhibition of HPV 16 E6-expressing cells by an adenovirus-expressing p53 homologue p73beta. *Oncogene* 2003, 22, 8394-402). A total of $1.5 \times 10^3$ cells/well were plated in a 96-well plate. After 24 h of plating, the cells were treated with indicated amounts of compounds. A measure of 20 µL (5 mg/mL) of MTT was added to each well 48 hrs after the addition of the compounds. MTT is a tetrazolium salt that is converted by living cells into purple formazan crystals. The medium was removed from the wells 3 hrs after MTT addition and 200 µL of DMSO (Dimethyl sulfoxide) was added to dissolve the formazan crystals, and then the absorbance was measured at 550 nm in an ELISA reader.

Example 5

Description of the Binding Site

The crystal structures of NMPRTase, in complex with the known inhibitor FK866/DGB, and reaction product NMN, reveal that the active enzyme exists as a dimer. The catalytic centre is present at the interface of the two chains. There are two active sites per dimer and residues from both the chains are involved in the interactions with the product NMN at each site. The binding pocket of the two ligands resembles a tunnel and involves mostly distinct residues, with NMN binding to one end and FK866 essentially spanning till the other end. However, some residues are common to both, indicating the overlap in their binding poses. An essential feature of both the binding poses is the presence of hydrophobic stacking in which an aromatic group in the ligand is sandwiched between the F193 of one subunit and Y18 of another subunit. The conservation of these interactions, especially the hydrophobic stacking, was used as a criterion for filtering docked ligands, subsequent to the selection on the basis of binding energy and cluster size. Sequence alignment of the human NMPRT, NAPRT (Nicotinic acid adenine phosphoribosyltransferase) and QPRT (quinolinate phosphoribosyltransferase) enzymes, performed with ClustalW, shows that they have diverged in terms of sequences considerably. Moreover, NAPRTase does not contain a tunnel at the dimer interface, which is actually the prime factor in the lack of inhibition of NAPRTases by FK866. Structural analyses however shows that they adopt the same fold, yet there is very little similarity in the binding site residues, both in terms of sequence as well as structural features. Hence design of specific inhibitors can be achieved.

Example 6

Identification and Analysis of Potential Compounds

In accordance with the inventive steps, as a control study, the enzyme's reaction product NMN as well as the known inhibitor, FK866 were docked to the protein, an exercise which resulted in reproducing the crystal structure poses for both compounds. Table 1a lists the interaction energies computed for the docked NMN and FK866 as well as the deviations from the crystallographic observed poses. The energy values computed for these control compounds were used as reference values for identifying possible ligands from the large compound library. All those compounds which exhibited interaction energies above this threshold or in other words indicated binding weaker than the control compounds were eliminated from the list for further analysis. The result of the virtual screening of the dataset is summarized in Table 1b.

TABLE 1

Summary of docking results;
(A) Docking of reference compounds to NMPRTase reproducing the crystal poses;
(B) An overview of results of virtual screening to the same protein molecule.

| | A | | | |
|---|---|---|---|---|
| | Biochemical energy of binding (kcal/mol) | AD4 docked (kcal/mol) | RMSD from crystal pose | # cluster |
| NMN | NA | −8.02 | 0.87 | 35 |
| FK866 | −9.25 | −8.63 | 0.77 | 16 |

TABLE 1-continued

Summary of docking results;
(A) Docking of reference compounds to NMPRTase reproducing the crystal poses;
(B) An overview of results of virtual screening to the same protein molecule.

| | | B | | | |
|---|---|---|---|---|---|
| | # ligands | Energy cut-off | # ligands above cut-off | Cluster size cut-off | Potential ligands |
| Maybridge HitFinder ™ | 13214 | <−8.5 kcal/mol | 34 | >15 | 6 |

NA—Not available
refers to the number

[[So, the number in the clusters refers to the total number of confirmations of the ligand that bind in the same orientation within the specified RMSD threshold and binding with the same energy. Thus, a cluster is defined as a unit of such similar confirmations. More the number in each cluster better is the accuracy and confidence of the predicted pose of the ligand molecule.]]

Further more, the selection of potential ligands was made on the analysis of ligand protein contacts for top ranking poses of every ligand and the docked poses were visualized for the interactions. Interactions conserved with NMN and FK866 binding were calculated and compared with that of the short listed compounds. The best poses were identified using the four criteria in the given order of preference i) largest cluster size ii) lowest binding energy iii) hydrogen bonds with the active site residues and iv) conservation of interactions with those from NMN/FK866 binding.

Figure 1A:
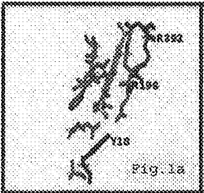
Figure 1B:
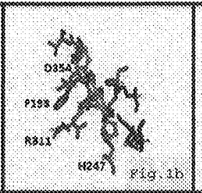
Figure 1C:
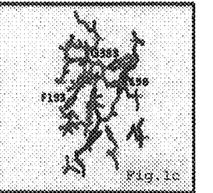
Figure 1D:
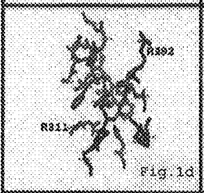
Figure 1E:
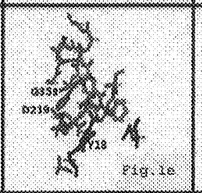
Figure 1F:
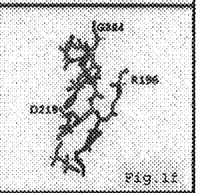
Figure 1G:
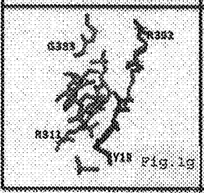
Figure 1H:
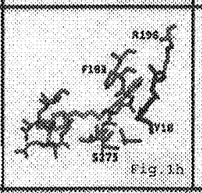
Figure 1I:
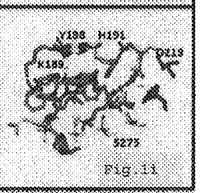
FIG. 1(i) shows the superposition of the FK866 site with the second mode site of compound 5. The ligands are in ball and stick model and colored by standard atom types; the A chain residues are shown in red and C chain residues are in blue, in all the panels. The residues in the A chain common between FK866 binding and second mode binding of compound 5 are shown in yellow sticks in FIG. 1(i).

As indicated in Table 1b, out of 13214 compounds screened, 34 compounds passed the energy threshold, of which top six compounds that were available were taken for further experimental testing which are shown in Table 2. The binding sites for both possible modes are shown in FIG. 1(a), FIG. 1(c) and FIG. 5. Interactions at the site for both possible modes are indicated in Table 2, and also in FIG. 5(a)-FIG. 5(f).

TABLE 2

Binding energy for six compounds and control compounds NMN and FK866 along with residues in each site. (The subscript refers to the residue number. Residues involved in hydrogen bond interactions are shown in boldface. The number in the clusters in the table refers to the total number of confirmations of the ligand that bind in the same orientation within the specified RMSD threshold and binding with the same energy. Thus, a cluster is defined as a unit of such similar confirmations. More the number in each cluster better is the accuracy and confidence of the predicted pose of the ligand molecule. The residues in the binding pocket column shows the amino acid residues of the protein molecule which are within 4Å radius of the docked ligand).

| Comp no. | Compound name and 2D-structure | Binding Free energy (kcal/mol) | Number in clusters | Residues in the binding pockets |
|---|---|---|---|---|
| 1 | Dipotassium 9-oxo-9H-fluorene-2,7-disulfonate  | −8.56 (Mode I) | 54 | $F_{193}$, $R_{196}$, $G_{197}$, $R_{311}$, $G_{353}$, $V_{356}$, $G_{384}$, $Y_{18}^1$, $T_{391}^1$, $R_{392}^1$, $D_{393}^1$ |
| | | −7.98 (Mode II) | 32 | $Y_{188}$, $H_{191}$, $F_{193}$, $D_{219}$, $V_{242}$, $A_{244}$, $A_{245}$, $S_{275}$, $I_{309}$, $R_{311}$, $I_{351}$, $Y_{18}^1$ |
| 2 | Ethyl-5-amino-6-cyano-7-(2-furyl)-4-oxo-3-phenyl-3,4-dihydro-1-phthalazinecarboxylate  | −9.45 (Mode I) | 44 | $F_{193}$, $R_{196}$, $D_{219}$, $E_{246}$, $H_{247}$, $R_{311}$, $D_{313}$, $G_{353}$, $D_{354}$, $G_{355}$, $V_{356}$, $G_{381}$, $S_{382}$, $G_{383}$, $G_{384}$, $G_{385}$, $D_{16}^1$, $Y_{18}^1$, $E_{149}^1$, $K_{415}^1$, $K_{423}^1$ |
| | | −8.12 (Mode II) | 14 | $Y_{188}$, $H_{191}$, $G_{217}$, $Y_{240}$, $S_{241}$, $V_{242}$, $P_{273}$, $P_{307}$, $I_{309}$, $R_{349}$, $V_{350}$, $I_{351}$, $I_{378}$, $A_{379}$, $Q_{92}^1$ |
| 3 | 1,[3,5-Di(2H-1,2,3-benzotriazol-2-yl)-2,4-dihydroxyphenyl]ethan-1-one  | −9.55 (Mode I) | 18 | $F_{193}$, $R_{196}$, $R_{311}$, $G_{353}$, $D_{354}$, $G_{355}$, $V_{356}$, $G_{381}$, $S_{382}$, $G_{383}$, $G_{385}$, $D_{16}^1$, $Y_{18}^1$, $R_{40}^1$, $R_{392}^1$, $D_{393}^1$, $N_{396}$ |
| | | −8.69 (Mode I) | 15 | $Y_{188}$, $K_{189}$, $H_{191}$, $F_{193}$, $G_{217}$, $D_{219}$, $Y_{240}$, $S_{241}$, $V_{242}$, $A_{244}$, $S_{275}$, $I_{309}$, $R_{311}$, $R_{349}$, $V_{350}$, $I_{351}$, $E_{376}$, $N_{377}$, $I_{378}$, $A_{379}$, $Y_{18}^1$ |

TABLE 2-continued

Binding energy for six compounds and control compounds NMN and FK866 along with residues in each site. (The subscript refers to the residue number. Residues involved in hydrogen bond interactions are shown in boldface. The number in the clusters in the table refers to the total number of confirmations of the ligand that bind in the same orientation within the specified RMSD threshold and binding with the same energy. Thus, a cluster is defined as a unit of such similar confirmations. More the number in each cluster better is the accuracy and confidence of the predicted pose of the ligand molecule. The residues in the binding pocket column shows the amino acid residues of the protein molecule which are within 4Å radius of the docked ligand).

| Comp no. | Compound name and 2D-structure | Binding Free energy (kcal/mol) | Number in clusters | Residues in the binding pockets |
|---|---|---|---|---|
| 4 | 7a-methyl-2,4,5-triphenyl-7,7a-dihydrocyclopenta[b]pyran-7-one | −8.56 (Mode I) | 40 | $F_{19}^{I}$, $R_{196}$, $H_{247}$, $G_{353}$, $D_{354}$, $G_{355}$, $V_{356}$, $G_{381}$, $S_{382}$, $G_{383}$, $G_{384}$, $G_{385}$, $Y_{18}^{1}$, $R_{40}^{1}$, $R_{392}^{1}$, $S_{398}^{1}$, $K_{415}^{1}$, $K_{423}^{1}$ |
|  |  | −8.23 (Mode I) | 27 | $Y_{188}^{1}$, $K_{189}$, $H_{191}$, $Y_{240}$, $S_{241}$, $V_{242}$, $P_{307}$, $I_{309}$, $R_{349}$, $V_{350}$, $E_{376}$, $I_{378}$, $A_{379}$ |
| 5 | 3-amino-2-benzyl-7-nitro-4-(2-quinolyl)-1,2-dihydroisoquinolin-1-one | −10.50 (Mode I) | 38 | $F_{193}$, $R_{196}$, $D_{219}$, $A_{244}$, $H_{247}$, $R_{311}$, $D_{313}$, $G_{353}$, $D_{354}$, $G_{355}$, $V_{356}$, $Y_{18}^{1}$, $E_{149}^{1}$, $R_{392}^{1}$, $S_{398}^{1}$, $F_{399}^{1}$, $K_{415}^{1}$, $K_{423}^{1}$ |
|  |  | −9.84 (Mode I) | 16 | $G_{185}$, $Y_{188}$, $K_{189}$, $H_{191}$, $Y_{240}$, $S_{241}$, $V_{242}$, $S_{275}$, $I_{309}$, $R_{349}$, $I_{351}$, $E_{376}$, $A_{379}$ |
| 6 | N-[(5-methyl-2-phenyl-2H-1,2,3-triazol-4-yl)methyl]-2H-chromene-3-carboxamide | −9.86 (Mode I) | 16 | $F_{193}$, $R_{196}$, $D_{219}$, $V_{242}$, $A_{244}$, $S_{275}$, $G_{353}$, $D_{354}$, $G_{355}$, $V_{356}$, $G_{381}$, $S_{382}$, $G_{383}$, $G_{384}$, $G_{385}$, $D_{16}^{1}$, $Y_{18}^{1}$ |
|  |  | −9.64 (Mode I) | 10 | $Y_{188}$, $H_{191}$, $F_{193}$, $D_{219}$, $Y_{240}$, $S_{241}$, $V_{242}$, $A_{244}$, $S_{275}$, $I_{309}$, $I_{351}$, $Y_{18}^{1}$, $H_{90}^{1}$, $Q_{92}^{1}$ |
| 7 | CONTROL n-[4-(1-benzoylpiperidin-4-yl)butyl]-3-pyridin-3-ylpropanamide (FK866) | −8.63 | 16 | $F_{193}$, $G_{194}$, $Y_{195}$, $R_{196}$, $G_{197}$, $D_{219}$, $R_{311}$, $D_{313}$, $G_{353}$, $V_{356}$, $G_{384}$, $G_{385}$, $D_{16}^{1}$, $Y_{18}^{1}$, $R_{392}^{1}$, $D_{393}^{1}$ |

TABLE 2-continued

Binding energy for six compounds and control compounds NMN and FK866 along with residues in each site. (The subscript refers to the residue number. Residues involved in hydrogen bond interactions are shown in boldface. The number in the clusters in the table refers to the total number of confirmations of the ligand that bind in the same orientation within the specified RMSD threshold and binding with the same energy. Thus, a cluster is defined as a unit of such similar confirmations. More the number in each cluster better is the accuracy and confidence of the predicted pose of the ligand molecule. The residues in the binding pocket column shows the amino acid residues of the protein molecule which are within 4Å radius of the docked ligand).

| Comp no. | Compound name and 2D-structure | Binding Free energy (kcal/mol) | Number in clusters | Residues in the binding pockets |
|---|---|---|---|---|
| 8 | CONTROL Nicotinamide ribose monophosphate (NMN) | −8.02 | 27 | $F_{193}$, $R_{196}$, $G_{353}$, $D_{354}$, $G_{355}$, $V_{356}$, $D_{357}$, $G_{381}$, $S_{382}$, $G_{383}$, $G_{384}$, $G_{385}$, $K_{389}$, $R_{392}^{1}$, $D_{393}^{1}$ |

Example 7

Inhibition of NMPRTase Activity by Selected Lead Compounds

Figure 2A:
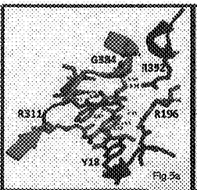
FIG. 2(A). Log 2-transformed gene expression ratios obtained from real-time quantitative PCR analysis are plotted for PBEF1. Each bar represents a data derived from the indicated cell line. In each sample, fold change in gene expression is calculated over its mean expression in normal brain samples.
Figure 2B:
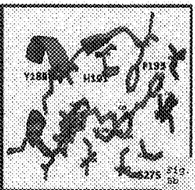
FIG. 2(B). Equal amounts of total protein lysates from indicated cell lines were subjected to western blotting to detect levels of PBEF1 and Tubulin proteins.

In accordance with the inventive steps, selected compounds were tested for inhibition of NMPRTase activity. Measurement of the ability of NMPRTase to convert 14[C]-nicotinamide to 14[C]-NAD was carried out. Most of the glioblastoma tissues have elevated levels of transcript and protein of PBEF1/NMPRTase. To prepare NMPRTase enzyme, firstly a panel of glioma derived cell lines was tested for NMPRTase transcript and protein levels. Out of seven glioma cell lines tested, two cell lines, U87 and U138, had substantially high levels of PBEF1 transcripts in comparison to normal brain samples (FIG. 2 A). Western blotting analysis also corroborated above results that U87 and U138 had relatively higher levels of PBEF1/NMPRTase protein levels (FIG. 2 B).

Figure 2C:
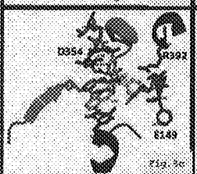
FIG. 2(C). NMPRTase assay was carried out as described in the methods section with extracts obtained from U87 or U251 cells either with or without the FK866.
Figure 2D:
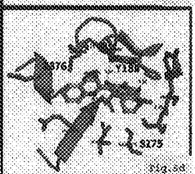
Figure 2E:
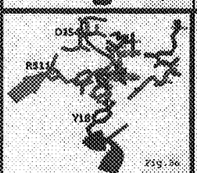
Figure 2F:
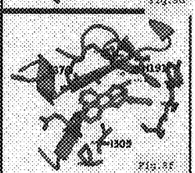
Figure 3A:
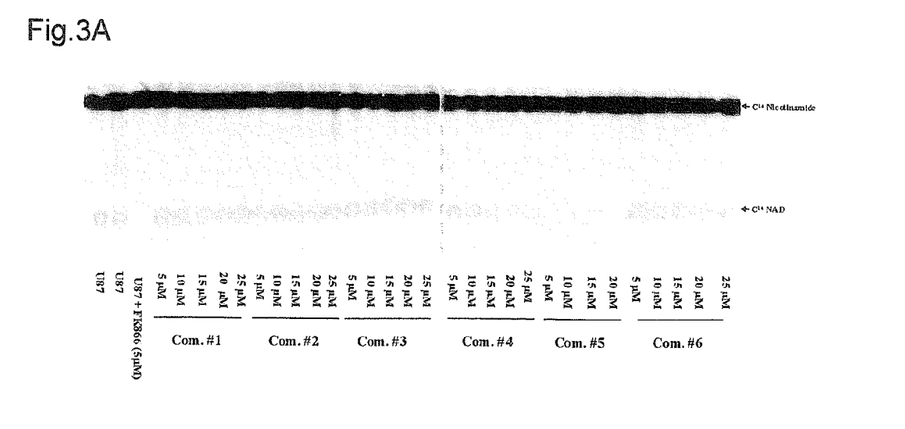
FIG. 3(A). NMPRTase assay was carried out as described in the methods section with extracts obtained from U87 with indicated amounts of either FK866 or compound 1 to 6.
Figure 3B:
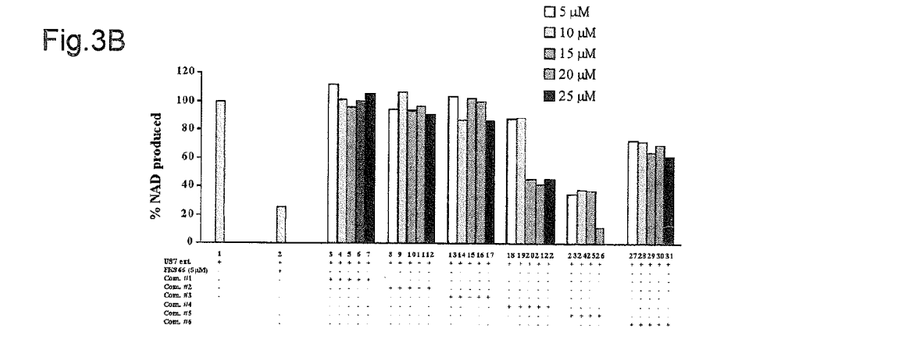
FIG. 3(B). The amount of $C^{14}$NAD+ formed in the experiment described above (A) is measured and shown. Please note that compound 5 and 4 inhibited the NMPRTase activity.

U87 cells were chosen as the source of NMPRTase. The NMPRTase enzyme extract from U87 converted the 14[C] labeled nicotinamide to NAD (FIG. 2C lane 1). FK866, the known inhibitor of NMPRTase inhibited efficiently this reaction (FIG. 2C compare lane 2 with 1). As expected, the extract from U251 cells, which had very low levels of PBEF1 transcript and protein, did not convert 14[C] labeled nicotinamide to NAD (FIG. 2C lane 3). Then testing the ability of six selected lead compounds to inhibit NMPRTase activity was done. Out of six compounds, compounds 4 and 5 inhibited NMPRTase activity (FIGS. 3A and B). Com 5 was found to be more potent in NMPRTase inhibition (FIGS. 3 A and B compare lanes 23-26 with lanes 1 and 2).

Example 8

Inhibition of Growth PBEF1 Over Expressing Glioblastoma Cell Line U87

Figure 4:
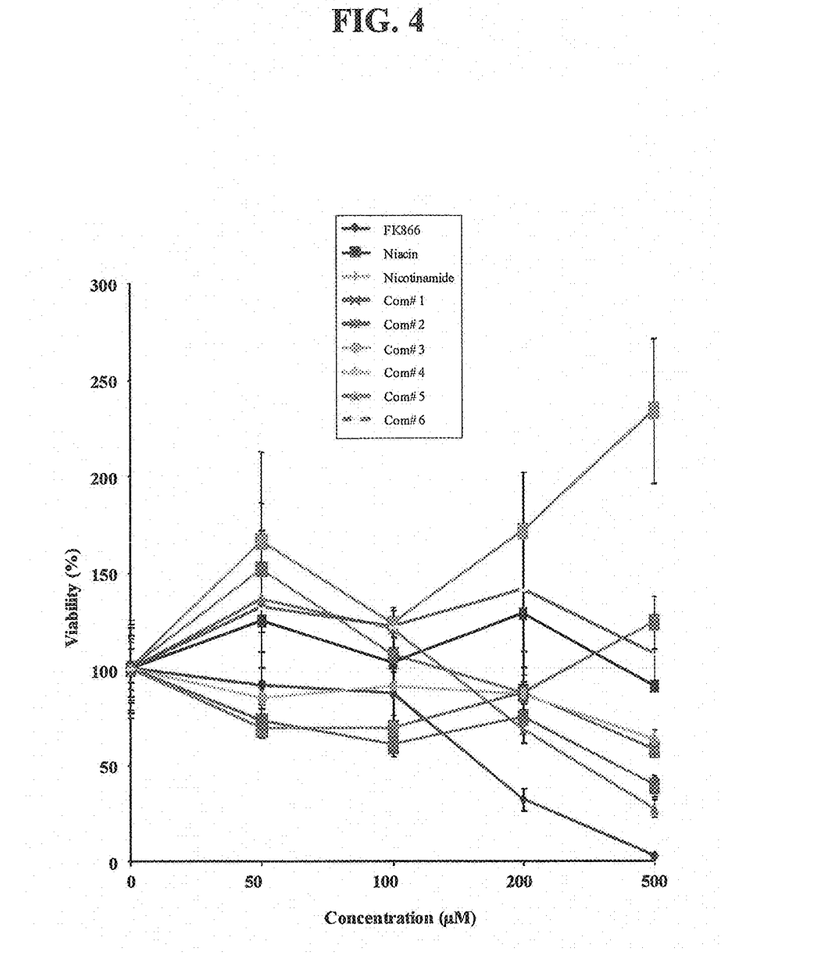
FIG. 4:
Viability was measured by MTT assay at 48 hrs after addition of indicated compounds to U87 cells. The assays were carried out in triplicates and the mean value for each time point was used to generate the graph.

In accordance with the inventive steps, to correlate the NMPRTase inhibition property with cell growth inhibition, the ability of these compounds to inhibit the growth of a glioma derived cell line U87 was tested, which has elevated levels of PBEF1. FK866, the known NMPRTase inhibitor, inhibited the growth of U87 cells efficiently with an IC50 of 170 μM (FIG. 4 and Table 3). Of the six selected lead compounds, compounds 1 and 5 only inhibited the growth of U87 with an IC50 of 335 and 325 μM respectively (FIG. 4 and Table 3). Since the compound 1 did not inhibit NMPRTase activity (FIGS. 3A and 3B), it might utilize a different mechanism to inhibit the growth of U87 cells. However, compound 5, which inhibited NMPRTase activity as well as the growth of U87 cells, emerges as a potent inhibitor of NMPRTase and cancer cell growth.

TABLE 3

List of compounds and their IC50 (half maximal inhibitory concentration) values.

| Compound Name | $IC_{50}$ (μM) |
|---|---|
| FK866 | 170 |
| Niacin | >500 |
| Nicotinamide | >500 |
| Compound 1 | 335 |
| Compound 2 | >500 |
| Compound 3 | >500 |
| Compound 4 | >500 |
| Compound 5 | 325 |
| Compound 6 | >500 |

We claim:

1. A method for treating glioblastoma multiforme, wherein the said method comprising administrating to the patient suffering from glioblastoma multiforme cancer the compound 3-amino-2-benzyl-7-nitro-4-(2-quinolyl)-1,2-dihydroisoquinolin-1-one represented by formula A.

Formula A

2. The method as claimed in claim 1, wherein the said compound acts as inhibitor of NMPRTase (nicotinamide phosphoribosyl transferase) enzyme useful for regulating growth of glioma cells.

3. The method as claimed in claim 1, wherein the said compound has energy cut-off value of less than −8.5 kcal/mol and cluster size cut-off value of more than 15.

4. The method as claimed in claim 1, wherein the glioma cells used is gliomablastoma cell line U87.

5. The method as claimed in claim 1, wherein the compound 3-amino-2-benzyl-7-nitro-4-(2-quinolyl)-1,2-dihydroisoquinolin-1-one inhibits glioma derived cell line U87 with $IC_{50}$ of 325 μM in vitro.

\* \* \* \* \*